(12) United States Patent
Withall (10) Patent No.: US 6,189,870 B1
(45) Date of Patent: Feb. 20, 2001

(54) DUAL PORT MEDICAL OXYGEN HUMIDIFIER

(76) Inventor: Gordon Withall, 17471 Bonner Dr., Tustin, CA (US) 92680

( * ) Notice: Under 35 U.S.C. 154(b), the term of this patent shall be extended for 0 days.

(21) Appl. No.: 09/285,138

(22) Filed: Apr. 1, 1999

Related U.S. Application Data (63) Continuation-in-part of application No. 08/886,191, filed on Jul. 1, 1997, now abandoned.

(51) Int. Cl.⁷ ............................................ B01F 3/04
(52) U.S. Cl. .................... 261/62; 261/63; 261/121.1; 128/203.12; 128/203.22; 128/204.14
(58) Field of Search .................. 261/62, 63, 65, 261/121.1; 128/203.12, 203.16, 203.22, 203.24, 204.14

(56) References Cited

U.S. PATENT DOCUMENTS

| | | | |
|---|---|---|---|
| 2,572,199 | * 10/1951 | Richards | 261/63 |
| 2,613,067 | * 10/1952 | Goodyer | 261/63 |
| 2,941,528 | * 6/1960 | Fabian et al. | 128/204.14 |
| 3,107,689 | * 10/1963 | Schreiber et al. | 128/204.14 |
| 3,192,924 | * 7/1965 | Edmondson et al. | 261/63 |
| 4,067,935 | * 1/1978 | Jones et al. | 261/65 |
| 4,607,634 | * 8/1986 | Clapham | 128/204.14 |

FOREIGN PATENT DOCUMENTS

| | | | |
|---|---|---|---|
| 775368 | * 1/1968 | (CA) | 128/204.14 |
| 1149860 | * 6/1963 | (DE) | 128/204.14 |
| 133194 | * 12/1960 | (SU) | 128/204.14 |
| 193692 | * 6/1967 | (SU) | 128/204.14 |
| 379270 | * 6/1973 | (SU) | 128/204.14 |

* cited by examiner

Primary Examiner—C. Scott Bushey
(74) Attorney, Agent, or Firm—John D. Gugliotta (57) ABSTRACT

An improved disposable bubble oxygen humidifier is provided having a humidifying chamber included for the blending of oxygen and moisture. A slide switch on the top of the humidifier directs pure oxygen to the patient, or alternately, routes the oxygen through the humidifier and on to the patient. Hoses are attached at an inlet supply port and an outlet discharge port.

7 Claims, 9 Drawing Sheets

DUAL PORT MEDICAL OXYGEN HUMIDIFIER

RELATED APPLICATIONS

The present invention is a Continuation-in-Part of a U.S. patent application Ser. No. 08/886,191. filed Jul. 1, 1997, now abandoned.

BACKGROUND OF THE INVENTION

1. Field of the Invention

The present invention relates generally to medical oxygen humidifiers and, more particularly, to a dual port medical oxygen humidifier capable of switching between dry and humidified oxygen rapidly.

2. Description of the Related Art

Medical oxygen is delivered to patients in a variety of medical settings, such as hospitals, nursing homes, and other medical institutions. As conventionally utilized, such oxygen specifically for patient use needs to be humidified when the delivery from the source to the patient is set above two or three liters per minute (LPM). Such oxygen flow rates are generally known to dry out sensitive nasal and bronchial tissues, and humidification of the delivered oxygen has been used to mitigate such problems. The delivery of oxygen at these flowrates, and therefore the humidification, are generally used in a number of known situations, such as for certain chronic and acute respiratory diseased patients, for oncology patients, for postoperative heart patients, for neonatal patients, and for home health care patients.

In other situations a respiratory therapist must administer nebulized medicated inhalation treatments requiring a higher flow rate of non-humidified oxygen.

Presently available disposable oxygen humidifiers are not known to be equipped to switch from humidified oxygen to straight oxygen. In order to overcome this deficiency, the therapist must perform a five step operation including shutting off the oxygen flow, unscrewing the humidifier, screwing on to the flow meter a tapered tube adapter, pushing the nebulizer tubing onto the tapered adapter, and then restarting the oxygen flow. When the treatment is completed, the therapist then reverses these five steps in order to return the flow of humidified oxygen. This entire ten-step operation can take as long as five minutes, and leaves the patient with no oxygen support in the interim.

Another problem occurs when breaks occur in a closed oxygen deliver system. Contamination and cross contamination are possible, and made more likely. Because of this, disposable humidifiers should be disposed of every 12 to 48 hours, depending on the critical nature of the patient.

A search of the prior art did not disclose any patents that read directly on the claims of the instant invention; however, the following references were considered related:

| U.S. Pat. No. | Inventor | Issue Date |
| --- | --- | --- |
| 5,407,604 | Douglas Luffman | Apr. 18, 1995 |
| 5,396,884 | James T. Bagwell et al. | Mar. 14, 1995 |
| 4,993,411 | James J. Callaway | Feb. 19, 1991 |
| 4,753,758 | Kenneth G. Miller | Jun. 28, 1988 |
| 4,603,021 | Charles L. Urso | Jul. 29, 1986 |
| 4,532,088 | Kenneth G. Miller | Jul. 30, 1985 |
| 4,381,267 | Richard R. Jackson | Apr. 26, 1983 |
| D338,519 | Terry A. Peterson | Aug. 17, 1983 |
| D263,337 | Richard E. Hart et al. | Mar. 9, 1982 |

Of particular importance is Patent Number D263,337, in which an ornamental variation of the most typical disposable medical oxygen humidifier is disclosed.

Some devices in the prior art are constructed strictly for administering anesthetic gasses. None permit administration of either oxygen or humidified oxygen in the functional manner disclosed by the present invention.

Another problem found prevalent in the prior art is that the adjustment mechanisms are small in size, thereby making it difficult for nurses and other health care professionals with lowered finger and hand dexterity to adjust the device.

Consequently, a need has therefore been felt for an improved but less complex mechanism that can allow a respiratory therapist to easily switch between humidified oxygen delivery and straight oxygen delivery. Such reduced handling of the present invention reduces or eliminates the possibility of passing off nosocomial and drug resistant infections to the patient.

SUMMARY OF THE INVENTION

It is therefore an object of the present invention to provide an improved medical oxygen humidifier that is quick, easy and foolproof to use.

It is a feature of the present invention to provide an improved medical oxygen humidifier that can be quickly and easily switched from humidified oxygen to straight oxygen.

Briefly described according to one preferred embodiment, the present invention is designed as an improvement on the commonly used, disposable bubble oxygen humidifier. A humidifying chamber is included for the blending of oxygen and moisture. A slide switch on the top of the humidifier directs pure oxygen to the patient, or alternately, routes the oxygen through the humidifier and on to the patient. Hoses are attached at an inlet supply port and an outlet discharge port in an otherwise conventional manner.

An advantage of the present invention is that no oxygen deprivation is experienced when switching between humidified oxygen to straight oxygen.

Another advantage of the present invention is that the risk of cross contamination is decreased when switched between humidified oxygen and straight oxygen.

Further, a preferred embodiment of the present invention can result in less lowering of patient oxygenation rate, decreases in patient respiratory or cardiac stress, and decreased replacement cost of humidifiers and tubing due to cross contamination.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
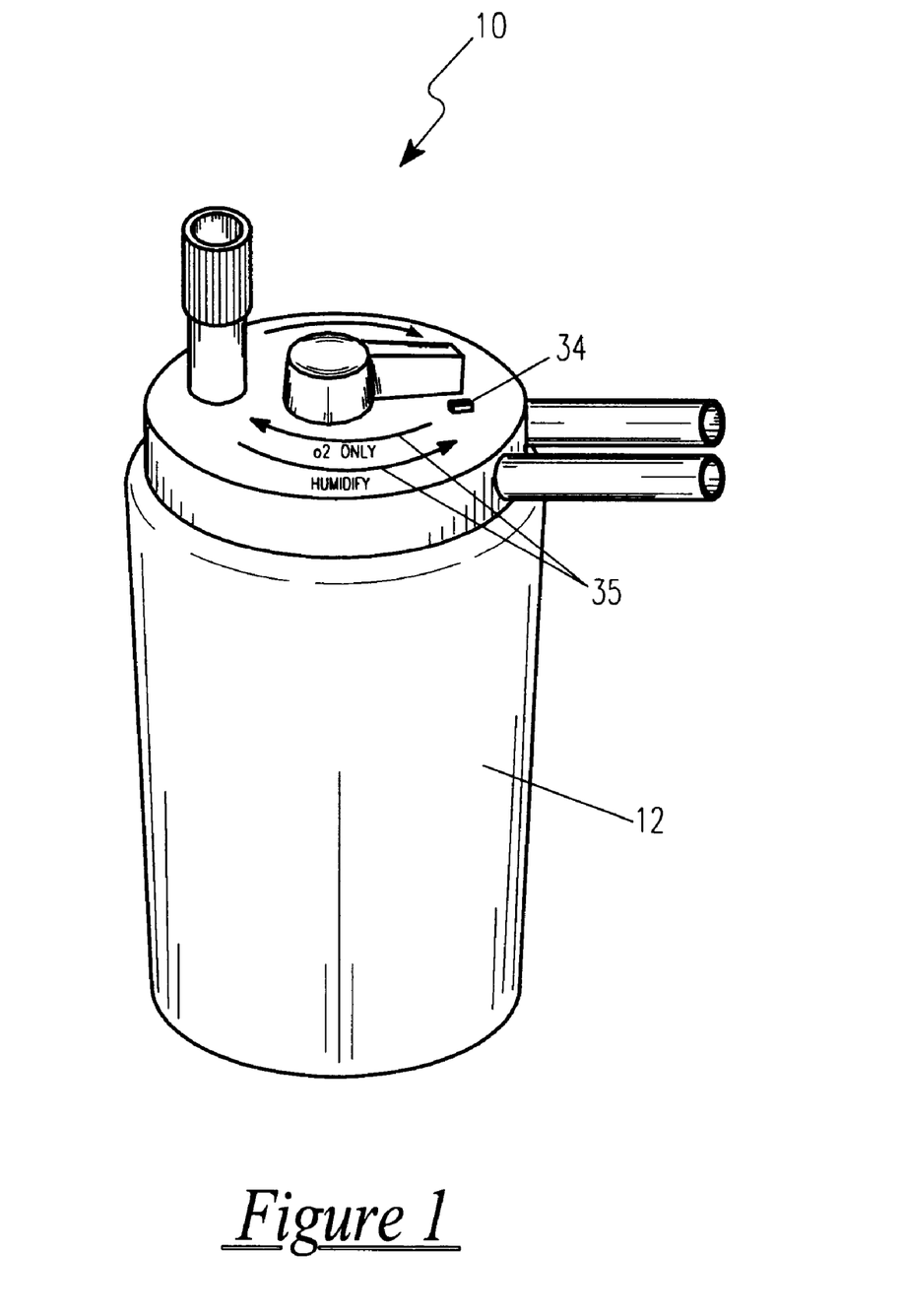
FIG. 1 is a perspective view of an improved oxygen humidifier according to the preferred embodiment of the present invention.
Figure 2:
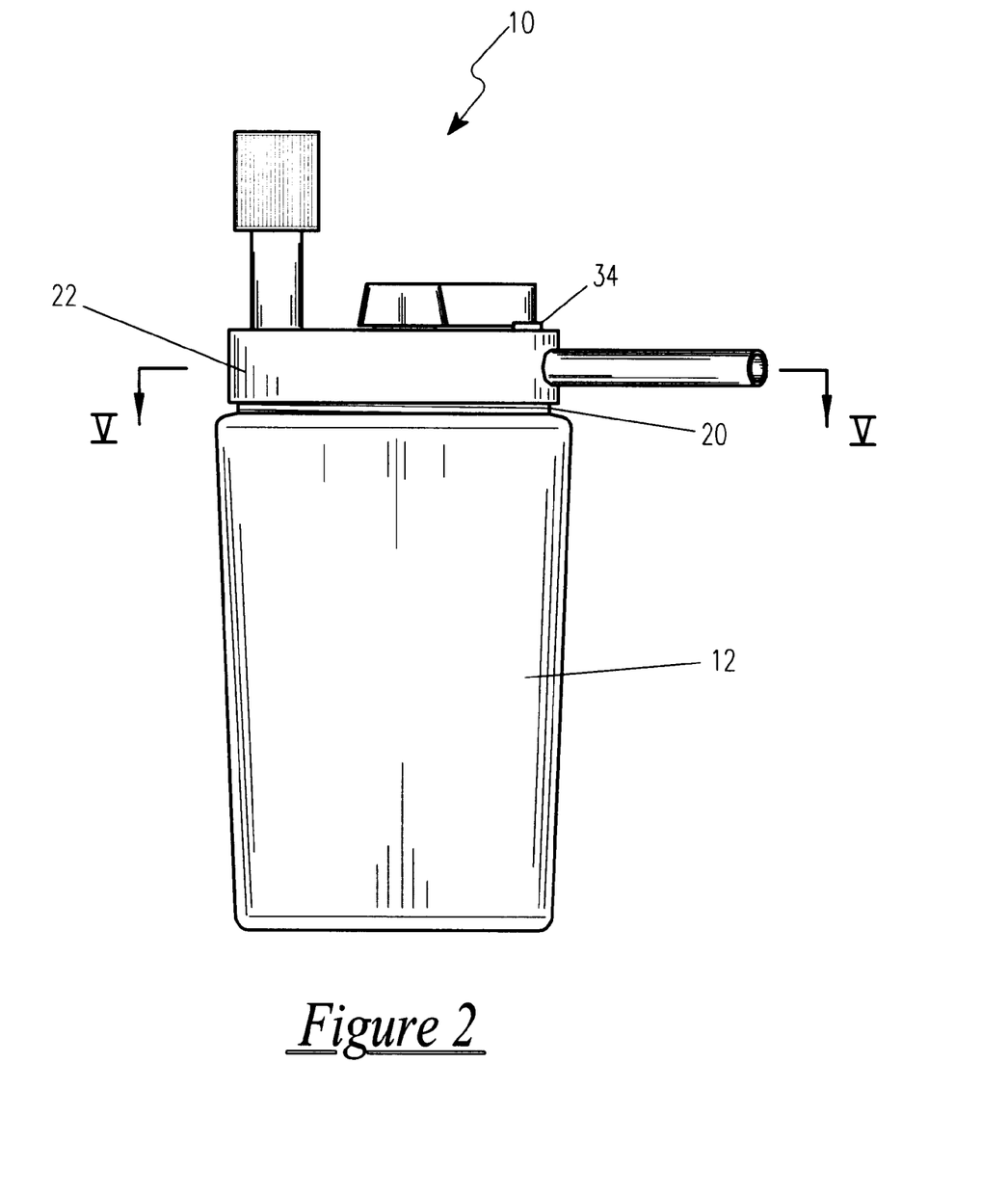
FIG. 2 is a side elevational view thereof.

Referring now to FIG. 1, an improved medical oxygen humidifier, generally noted as 10, is shown according to the preferred embodiment of the present invention. Although the teachings of this disclosure could be easily adaptable to other specific embodiments by one skilled in the art, it is felt that a sufficient embodiment would be based upon improvements to an already generally available disposable bubble oxygen humidifier. As such, a generally cylindrical humidifying chamber 12 is included for the blending of oxygen and moisture. As best shown in FIG. 2, the humidifying chamber 12 can be composed of a beaker or vessel forming an internal volume for holding humidifying fluid, and having a threaded upper opening 20 for affixing to an attachable lid 22. Although many materials of construction can be utilized and no single particular material is a necessary requisite to achieve the benefits of the present invention, a humidifying chamber of clear or translucent medical grade plastic will provide a lightweight, sanitary device that has been proven in numerous manufacturing methods and medical applications.

Figure 3:
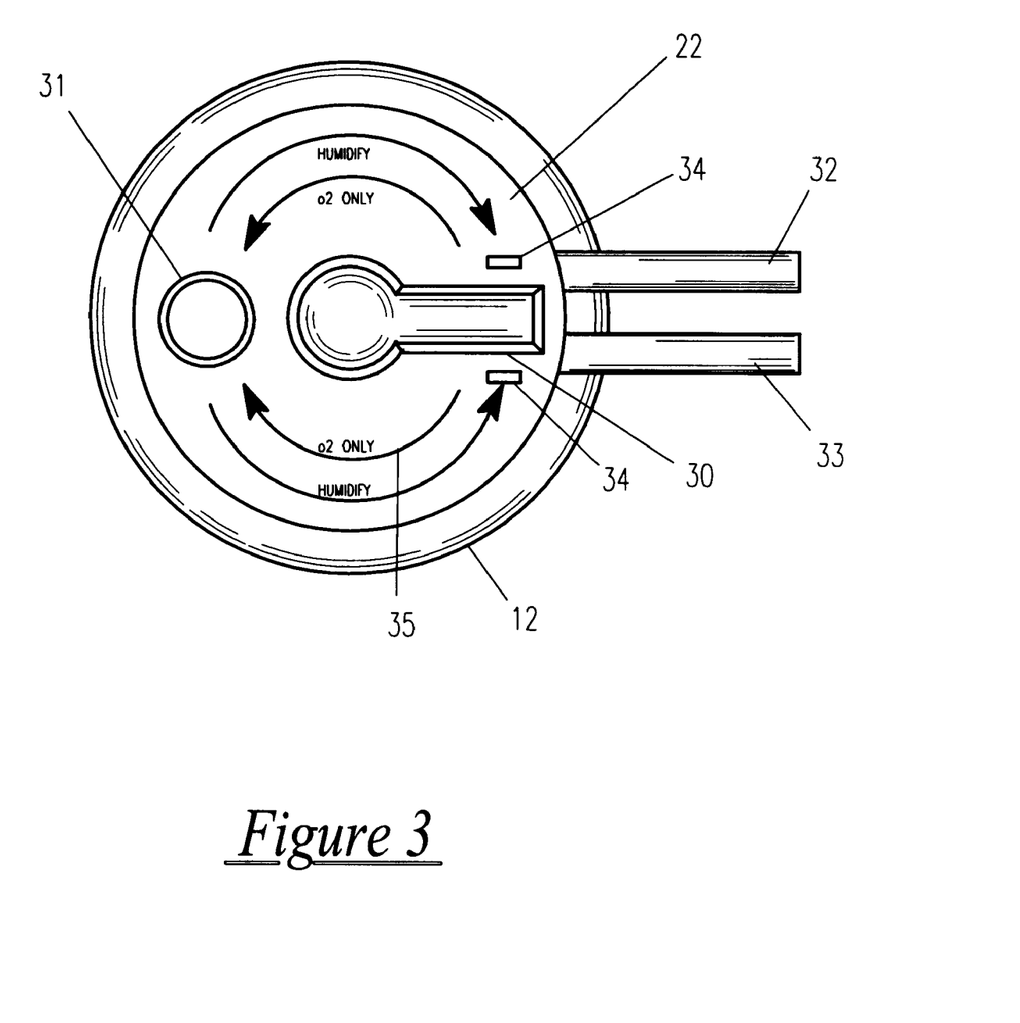
FIG. 3 is a top plan view thereof.

In conjunction with FIG. 3, the attachable lid 22 is shown in better detail. A slide switch 30 on the top of the humidifier lid 22 is designed to switch the flow of oxygen, either bypassing the humidifier chamber 12 directly and directing pure oxygen to the patient, or alternately, routing the oxygen through the humidifier and on to the patient. A plurality of hose ports are used for this function. Hoses are attached at an inlet supply port 31, a first outlet discharge port 32 for humidified oxygen, and a second outlet discharge port 33 for pure oxygen as described below.

Slide switch locking means 34 are used to lock the slide switch 30 in either the pure oxygen only position or the humidified oxygen position. For purposes of disclosure, the slide switch locking means 34 is depicted as linearly elongated protrusions, positioned on the top of the lid, and designed to allow the slide switch 30 to come into mechanical interference with the slide switch locking means 34 so that the slide switch 30 passes over either slide switch locking means 34, but remains on the outside of the slide switch locking means 34 due to slight frictional interference. Thus, the slide switch locking means 34 releasably locks the slide switch 30 in one of two positions. In one position, the present invention allows only pure oxygen to flow. In the other position, humidified oxygen flows.

Slide switch indicia 35 are positioned on the present invention to instruct the operator how to turn the slide switch 30 to effectuate the discharge of either pure oxygen or humidified oxygen.

Figure 4:
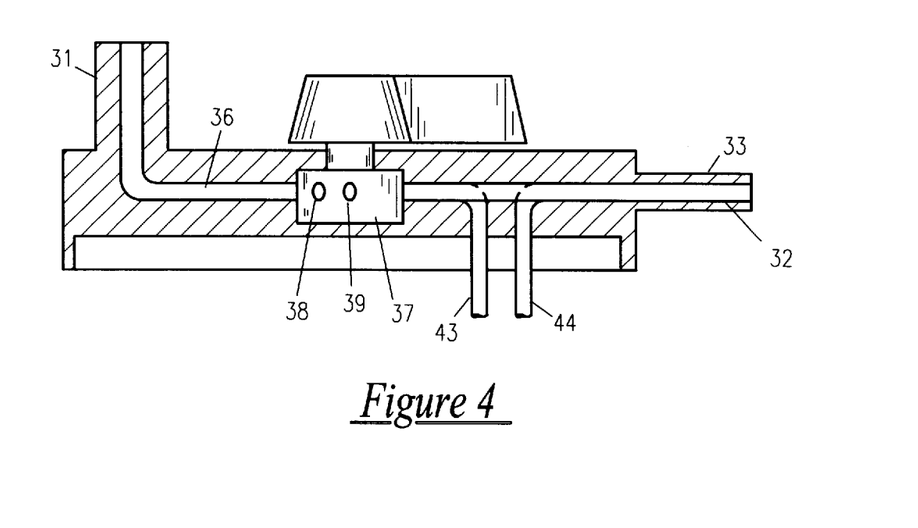
FIG. 4 is a cross sectional view of the preferred embodiment, cut along line IV—IV of FIG. 3.
Figure 5A:
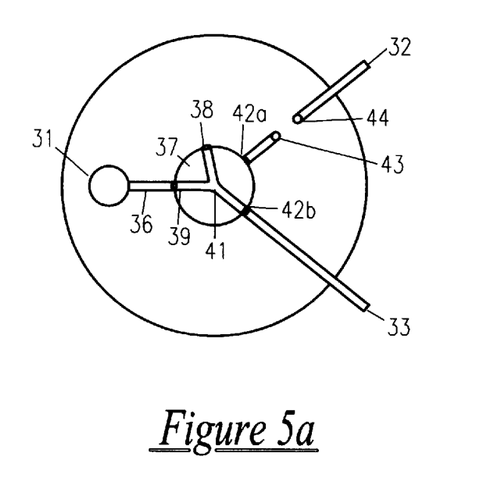
FIGS. 5a and 5b are cross sectional views of the preferred embodiment, cut along line V—V of FIG. 2, showing the oxygen path and method of use of the present invention.
Figure 5B:
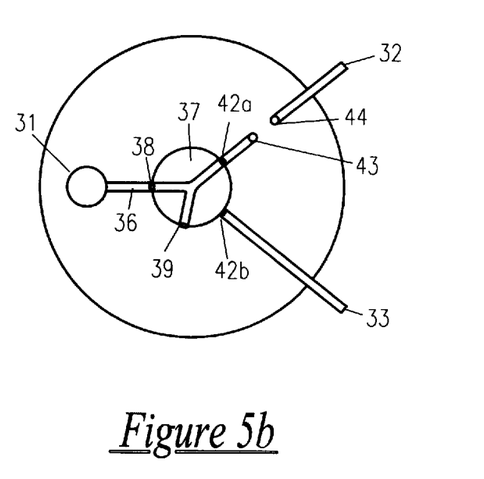

Referring now to FIGS. 4, 5a and 5b, the oxygen switching mechanism, which controls the flow of oxygen and humidified oxygen to the patient is disclosed.

In the preferred embodiment, an oxygen inlet channel 36 is located inside of the lid, and runs from the inlet supply port 31 to an oxygen transfer cylinder 37.

The oxygen transfer cylinder 37 is of a generally upstanding, cylindrical configuration, with a first cylinder inlet hole 38 and a second cylinder inlet hole 39. The oxygen transfer cylinder is seated in a cavity 40. The cavity 40 if of a generally cylindrical configuration, and is configured and sized so that the unused cylinder inlet hole rests against the interior wall of the cavity 40, thereby blocking oxygen flow out from the unused cylinder inlet hole.

The interior of the oxygen transfer cylinder 37 is generally solid, with a generally y-shaped channel 41, which directs oxygen out a first cylinder outlet hole 42a to the first discharge port 32 when the first cylinder inlet hole 38 is aligned with the oxygen inlet chamber 36. The generally y-shaped channel 41 directs oxygen out a second cylinder outlet hole 42b when the second cylinder inlet hole 39 is aligned with the oxygen inlet chamber 36. The oxygen transfer cylinder 37 is attached to the slide switch 30 so that by rotating the slide switch 30, the oxygen transfer cylinder 37 rotates, and one of the cylinder inlet holes 38, 39 aligns with the oxygen inlet channel 36. Also, the rotation of the oxygen transfer cylinder 37 moves the cylinder outlet hole 39 into fluid communication with either the first outlet discharge port 32 or the second outlet discharge port 33.

If pure oxygen is desired, the operator rotates the slide switch 30 clockwise so that the second cylinder inlet hole 39 aligns with the inlet channel 36 and the second cylinder outlet hole 42b aligns with the second outlet discharge port 33. If humidified oxygen is desired, the operator rotates the slide switch 30 counterclockwise, aligning the first cylinder inlet hole 38 with the inlet channel 36 and the first cylinder outlet hole 42a aligns with the first outlet discharge port 32.

A humidifying entry tube 43, of a generally linearly elongated, hollow configuration, is attached to and in fluid communication with the first cylinder outlet hole 42a. The humidifying entry tube 43 is located inside the lid 22. The humidifying entry tube 43 extends downward into the humidifying fluid located in the humidifier chamber 12. In this manner, oxygen passes through the oxygen inlet chamber 36, into the oxygen transfer cylinder 37 and into the humidifier chamber 12, thus creating bubbles which creates humidified oxygen.

A humidifying exit tube 44, of a generally linearly elongated, hollow configuration, is attached to and in fluid communication with the exterior end of the first outlet discharge port 32. The humidifying exit tube 44 is located inside the lid 22, and in closer proximity to the outer circumferential surface of the lid 22 than the humidifying entrance tube 43. The humidifying exit tube 44 extends downward from the lid 22, inside the humidifier chamber 12, but does not come into contact with the humidifying fluid. The humidifying exit tube 44 acts as a pressurized release channel for the humidified oxygen in the humidifying chamber 12.

Figure 6:
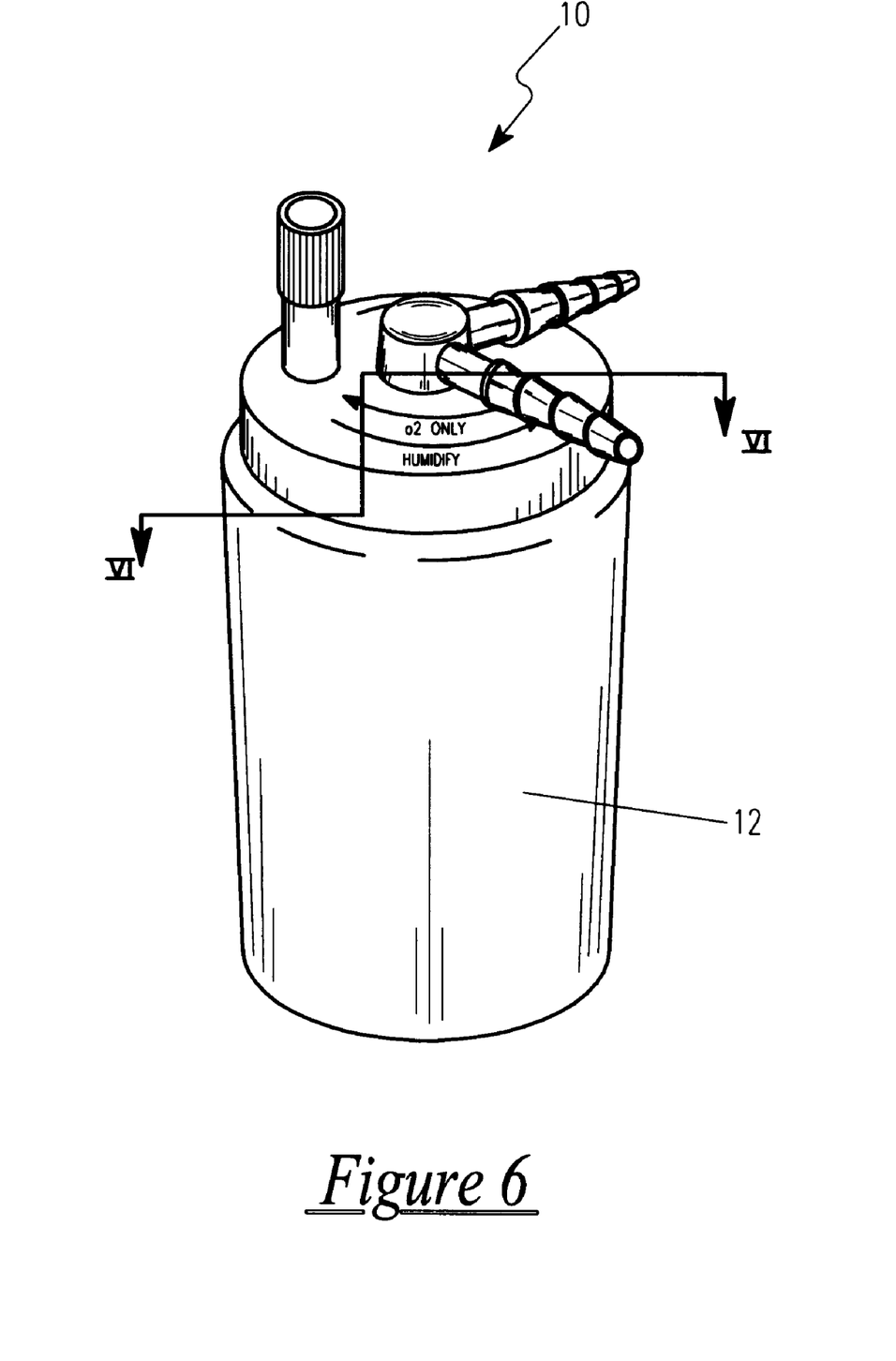
FIG. 6 is a perspective view of an alternate embodiment of the present invention.
Figure 7:
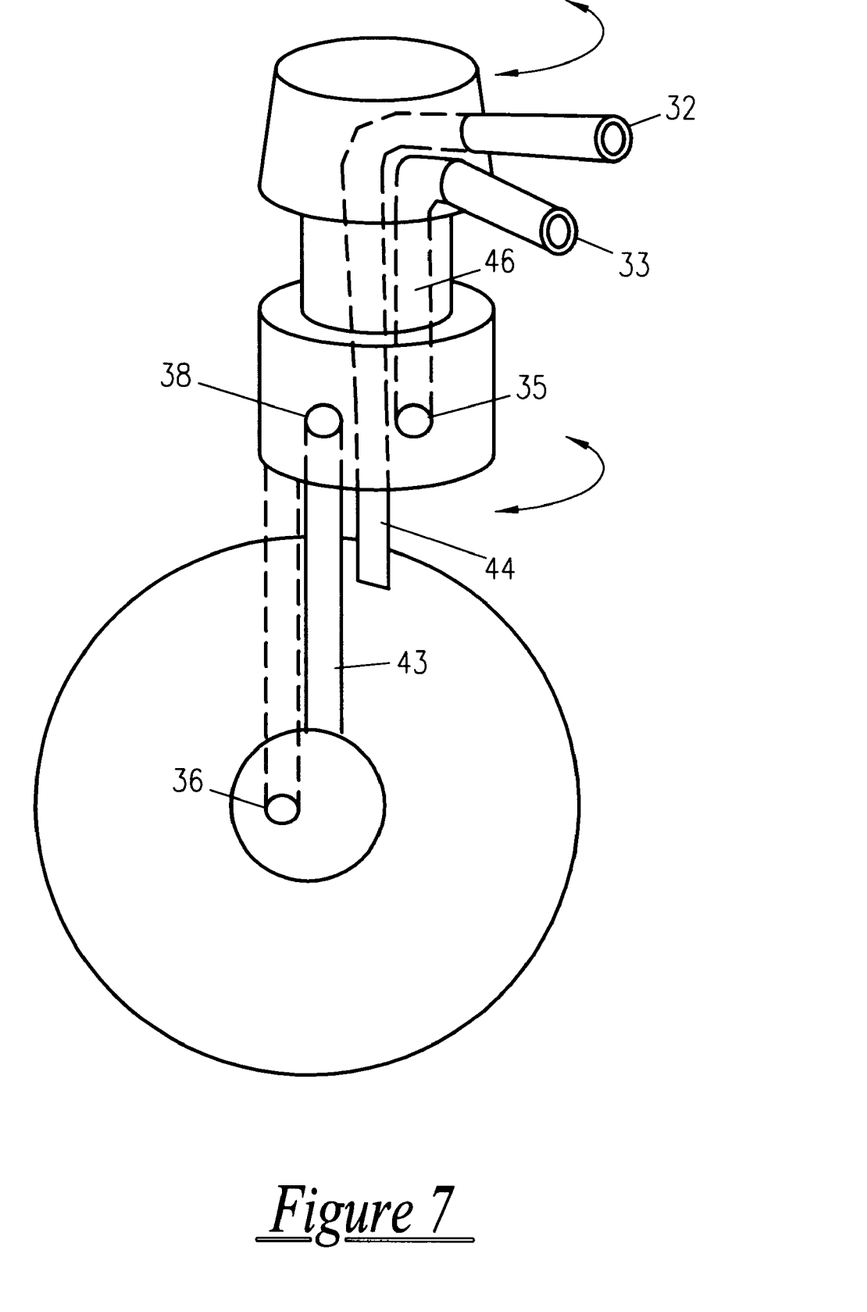
FIG. 7 is an exploded view of the alternate embodiment.
Figure 8:
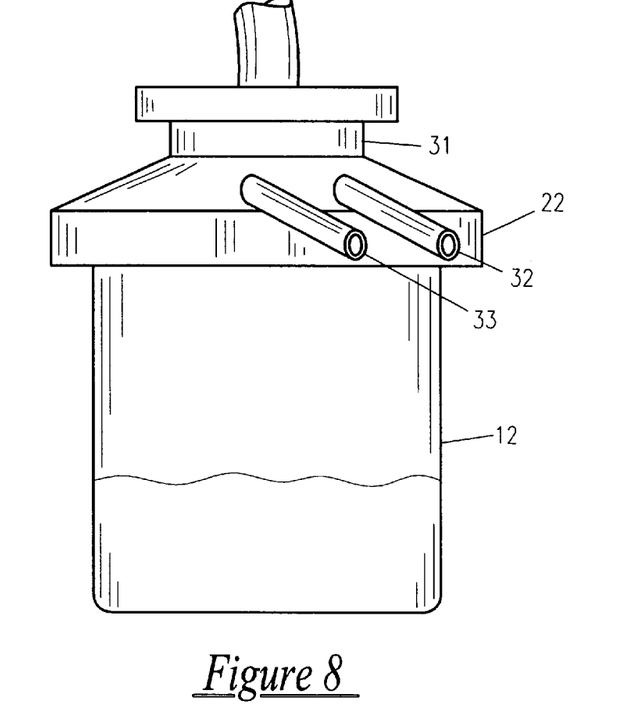
FIG. 8 is a perspective view of another alternate embodiment of the present invention.
Figure 9:
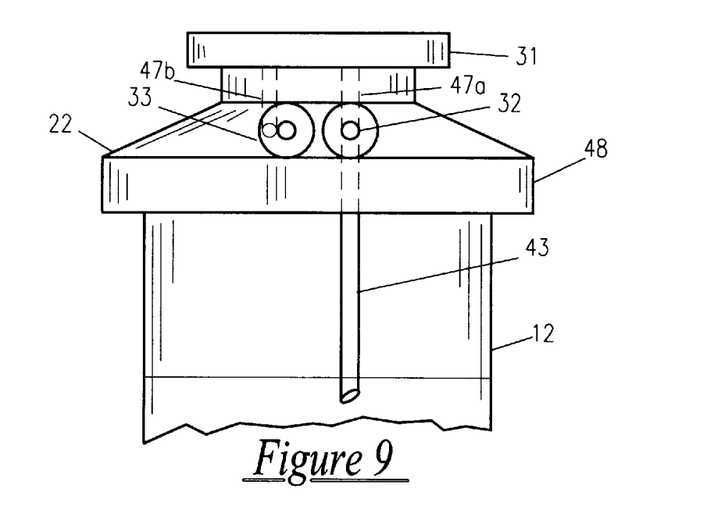
FIG. 9 is a cross sectional view of another alternate embodiment, cut along line IX—IX of FIG. 8.
Figure 10A:
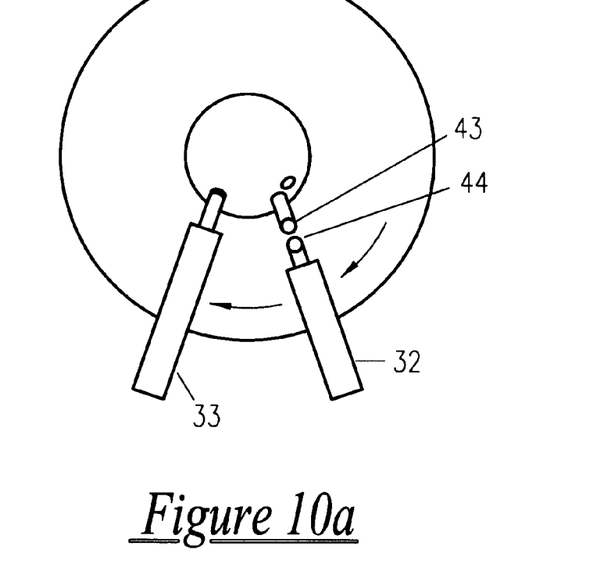
FIG. 10a and 10b are a series of cross sectional view of the alternate embodiment, cut along lines X—X of FIG. 8.
Figure 10B:
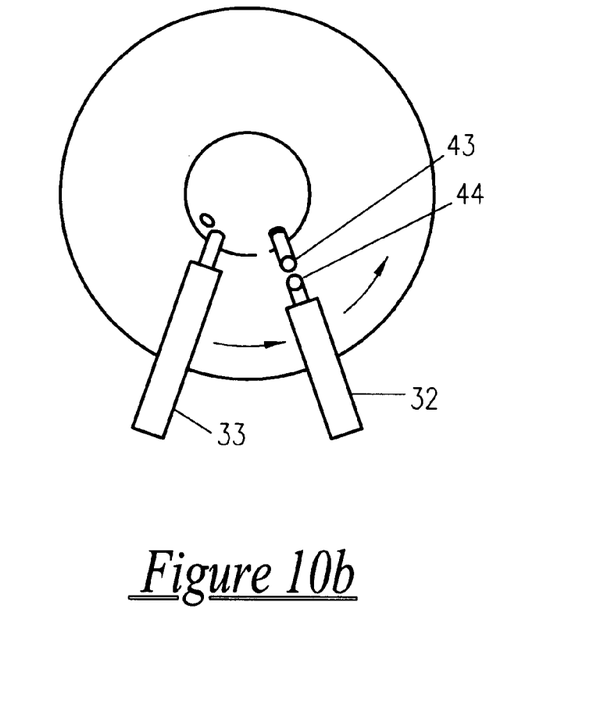

As shown in FIGS. 6 and 7, an alternate embodiment of the improved medical oxygen humidifier is shown. Herein, the attachable lid is shown in where the slide switch 30 on the top of the humidifier lid 22 is designed integral with the first outlet discharge port 33 for pure oxygen, and the second outlet discharge port 32 for humidified oxygen. To switch the flow of oxygen, either bypassing the humidifier chamber 12 directly and directing pure oxygen to the patient, or alternately, routing the oxygen through the humidifier chamber 12 and on to the patient, the user merely rotates the integrated slide switch 30, to which delivery hoses can be attached directly.

The internal mechanism of oxygen switching is identical to the preferred embodiment. However, by moving the position of the first outlet discharge port 32 and the second outlet discharge port 33 to the slide switch 30, requires slight adjustment of the tubing from the oxygen inlet channel 36.

A first cylinder tube 45 connects the first cylinder entry hole 38 to the first outlet discharge port 32. A second cylinder tube 46 connects the second cylinder entry hole 39 to the second outlet discharge port 33. The humidifying entrance tube 43 and the humidifying exit tube 44 are attached to the oxygen transfer cylinder 37. The humidifying entrance tube 43 is in fluid communication with the first cylinder entry hole 38 and the humidifying fluid in the chamber 12 and the humidifying exit tube 44 in fluid communication with the interior of the chamber 12 above the humidifying fluid, and the radially exterior end of the first outlet discharge port 32. Referring now to FIGS. 8, 9, 10a and 10b, another alternate embodiment of the present invention is disclosed. In this embodiment, a rotating portion 48 of the lid 22 having the first outlet discharge port 32 and the second outlet discharge port 33 attached thereto, is disclosed for switching the flow of oxygen, either bypassing the humidifier chamber 12 directly and directing pure oxygen to the patient, or alternately, routing the oxygen through the humidifier and directing humidified oxygen to the patient. A first and a second oxygen inlet channel 47a, 47b are present instead of one channel and are located within the lid 22. The first and second inlet channel 47a, 47b run from the inlet supply port 31 to the oxygen transfer cylinder 37. Rotating the rotating portion 48 of the lid 22 brings the first outlet discharge port 32 into alignment with the first oxygen inlet channel 47a for directing humidified oxygen to a patient. Further rotation of the rotation portion 48 of the lid 22 brings the second outlet discharge port 33 into alignment with the second oxygen inlet channel 47b for directing pure oxygen to the patient.

2. Operation of the Preferred Embodiment

Figure 11:
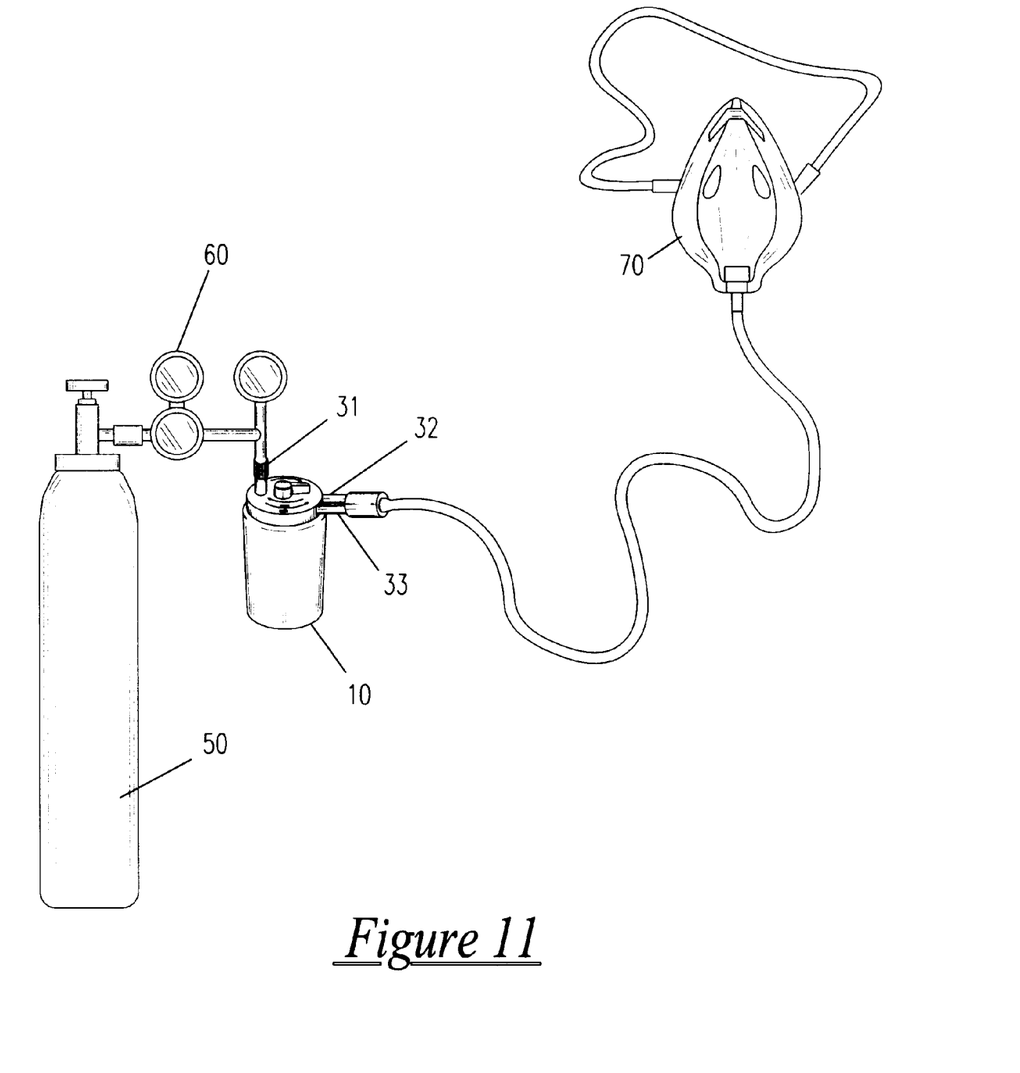
FIG. 11 is a perspective view of an oxygen tank and mask system in use with the present invention.

In accordance with a preferred embodiment of the present invention, as shown in FIG. 11, the medical oxygen humidifier 10 is used as part of an otherwise conventional oxygen delivery system. Oxygen is supplied in a portable manner utilizing a conventional portable oxygen cylinder 50, as shown, or can be supplied in conjunction with a wall mounted delivery system. The oxygen is regulated by a regulator 60 to control delivery rate, and is directed to an inlet supply port 31 via conventional medical grade tubing or other conduit means for providing fluid communication between the oxygen delivery system and the humidifier 10. Once delivered to the humidifier 10, a respiratory therapist or other qualified medical personnel can direct the oxygen flow either to the humidifying chamber 12, or to bypass the humidifying chamber 12 by use of the selector switch 30. Each of discharge nozzles 32, 33 can then be connected in fluid communication with a pair of separate oxygen receiving devices such as oxygen masks 70 or combined by a conventional "Y" fitting to the same oxygen receiving device. In this manner, a therapist or other user may switch instantly from humidified to pure oxygen, and then back again in a rapid, sanitary manner.

The foregoing description is included to illustrate the operation of the preferred embodiment and is not meant to limit the scope of the invention. The scope of the invention is to be limited only by the following claims.

What is claimed is:

1. An improved medical oxygen humidifier comprising:
   a generally cylindrical humidifying chamber forming an internal volume for holding humidifying fluid, said chamber further having a threaded upper opening;
   a lid, said lid having a top, and said lid being attachable to said threaded upper opening;
   an inlet supply port in fluid communication with said internal volume for attachment to an oxygen supply hose;
   a first outlet discharge port in fluid communication with said internal volume for discharging humidified oxygen;
   a second outlet discharge port in direct fluid communication with said inlet supply port for discharge of pure oxygen;
   a rotatable slide switch on said top of said lid in communication with said inlet supply port, said first outlet discharge port, and said second outlet discharge port, said slide switch for switching the flow of oxygen, either bypassing said humidifying chamber directly and directing pure oxygen to said second outlet discharge port, or alternately, routing the oxygen through said humidifying chamber and to said first outlet discharge port;
   a slide switch locking means, said slide switch locking means designed to secure said slide switch in one of two positions, corresponding to passage of non-humidified oxygen or humidified oxygen to a patient;
   slide switch indicia, said slide switch indicia designed to instruct an operator how to turn said slide switch to effectuate the discharge of either pure oxygen or humidified oxygen; and
   an oxygen switching assembly, said oxygen switching assembly designed to facilitate movement of pure oxygen from said inlet supply port to said second outlet discharge port and the movement of pure oxygen from said inlet supply port to the humidifying fluid in said chamber and then to said first outlet discharge port.

2. The improved medical oxygen humidifier described in claim 1, wherein said oxygen switching assembly further comprises;
   an oxygen transfer cylinder, of a generally upstanding, cylindrical configuration, said oxygen transfer cylinder attached to said slide switch and having a first cylinder inlet hole, a second cylinder inlet hole and a cylinder outlet hole;
   a cavity, said cavity formed within said lid, and designed to hold said oxygen transfer cylinder;
   an oxygen inlet channel, located inside of said lid, said oxygen inlet channel running from said inlet supply port to said oxygen transfer cylinder;
   a generally y-shaped channel, said y-shaped channel located inside of said oxygen transfer cylinder and designed to pass oxygen to either said first discharge port or said second discharge port, depending upon which of two cylinder inlet holes is aligned with said oxygen inlet channel;
   a humidifying entry tube, of a generally linearly elongated, hollow configuration, said humidifying entry tube attached to and in fluid communication with said cylinder outlet hole, located inside said lid, and extending downward into said humidifying fluid located in said humidifier chamber; and
   a humidifying exit tube, of a generally linearly elongated, hollow configuration, said humidifying exit tube attached to and in fluid communication with an exterior end of said first outlet discharge port, and said humidifying exit tube extending downward from said lid, inside said humidifying chamber, but not extending into contact with said humidifying fluid.

3. The improved medical oxygen humidifier described in claim 2, wherein said oxygen transfer cylinder is attached to said slide switch so that by rotating said slide switch, an oxygen inlet chamber rotates, and one of said cylinder inlet holes aligns with said oxygen inlet channel.

4. The improved medical oxygen humidifier described in claim 1, wherein if pure oxygen is desired, said operator rotates said slide switch clockwise so that said second cylinder inlet hole aligns with said inlet channel and said cylinder outlet hole aligns with said second outlet discharge port; if humidified oxygen is desired, said operator rotates said slide switch counterclockwise, aligning said first cylinder inlet hole with said inlet channel and said cylinder outlet hole with said first outlet discharge port.

5. The improved medical oxygen humidifier described in claim 1, wherein said humidifying chamber is composed of a beaker for holding humidifying fluid.

6. The improved medical oxygen humidifier of claim 1, wherein said humidifying chamber is comprised of clear or translucent medical grade plastic.

7. The improved medical oxygen humidifier described in claim 2, wherein said slide switch on said top of said humidifier lid is integral with said first outlet discharge port for humidified oxygen, and said second outlet discharge port for pure oxygen, such that to switch the flow of oxygen, either bypassing said humidifying chamber directly and directing pure oxygen to said patient, or alternately, routing the oxygen through said humidifier and on to said patient, said operator merely rotates an integrated slide switch, to which delivery hoses are directly attachable.

* * * * *